US012735701B2

(12) United States Patent
Lee et al.

(10) Patent No.: US 12,735,701 B2
(45) Date of Patent: Sep. 15, 2026

(54) TRANS-SPLICING RIBOZYME SPECIFIC TO APOE4 RNA AND USE THEREOF

(71) Applicant: RZNOMICS INC., Yongin-si (KR)

(72) Inventors: Seong-Wook Lee, Seoul (KR); Seung Ryul Han, Yongin-si (KR)

(73) Assignee: Rznomics Inc., Yongin-si (KR)

( * ) Notice: Subject to any disclaimer, the term of this patent is extended or adjusted under 35 U.S.C. 154(b) by 1189 days.

(21) Appl. No.: 17/626,656

(22) PCT Filed: Feb. 26, 2021

(86) PCT No.: PCT/KR2021/002443
§ 371 (c)(1),
(2) Date: Jan. 12, 2022

(87) PCT Pub. No.: WO2021/172925
PCT Pub. Date: Sep. 2, 2021

(65) Prior Publication Data

US 2025/0270547 A1 Aug. 28, 2025

(30) Foreign Application Priority Data

Feb. 28, 2020 (KR) ........................ 10-2020-0025332
Feb. 25, 2021 (KR) ........................ 10-2021-0025822

(51) Int. Cl.
*C12N 15/113* (2010.01)

(52) U.S. Cl.
CPC ........ *C12N 15/113* (2013.01); *C12N 2310/12* (2013.01); *C12N 2320/33* (2013.01)

(58) Field of Classification Search
CPC .............. C12N 15/113; C12N 2310/12; C12N 2320/33; A61P 25/28
See application file for complete search history.

(56) References Cited

U.S. PATENT DOCUMENTS

| | | | | |
|---|---|---|---|---|
| 2007/0248599 | A1 | 10/2007 | Tang | |
| 2010/0305197 | A1* | 12/2010 | Che | A61P 31/00 435/375 |
| 2019/0225969 | A1 | 7/2019 | Lee et al. | |

FOREIGN PATENT DOCUMENTS

| | | | |
|---|---|---|---|
| CN | 110268269 | A | 9/2019 |
| JP | 2007-530035 | A | 11/2007 |
| JP | 2009531299 | A | 9/2009 |
| KR | 2009-0118956 | A | 11/2009 |
| KR | 2013-0118671 | A | 10/2013 |
| WO | 2003048362 | A2 | 6/2003 |
| WO | 2005089539 | A1 | 9/2005 |
| WO | 2007/098417 | A2 | 8/2007 |
| WO | 2008097927 | A2 | 8/2008 |

OTHER PUBLICATIONS

Arboleda-Velasquez et al., "Resistance to autosomal dominant Alzheimer's diseases in an APOE3 Christchurch homozygote: a case report", Nature Medicine, vol. 25, Nov. 2019, pp. 1680-1683. (Year: 2019).*
Jackson et al., "Better Targeting, Better Efficiency for Wide-Scale Neuronal Transduction with the Synapsin Promoter and AAV-PHP-B", Frontiers in Molecular Neuroscience, Nov. 2016, vol. 9, Article 116. (Year: 2016).*
Hodes et al., "Alzheimer's "Prevention" vs. "Risk Reduction": Transcending Semantics for Clinical Practice", Frontiers in Neurology, Published Jan. 21, 2019, vol. 9, Article 1179, pp. 1-7. (Year: 2019).*
Love, J.E. et al. Alternative Splicing in Alzheimer's Disease. J. Parkinsons Dis. Alzheimers Dis. Aug. 2015, vol. 2, No. 2, inner pp. 1-12.
Lee, C.H. et al. Group I Intron-Based Therapeutics Through Trans-Splicing Reaction. Progress in Molecular Biology and Translational Science. 2018, vol. 159, pp. 79-100.
International Search Report issued in PCT/KR2021/002443, dated Jun. 18, 2021, 9 pages.
Mirna Safieh, et al., "ApoE4: an emerging therapeutic target for Alzheimer's disease", BMC Medicine, 2019, vol. 17, No. 64, 1-17 (17 pages).
Ioannis Papaioannou, et al., "Targeted In Situ Gene Correction of Dysfunctional APOE Alleles to Produce Atheroprotective Plasma ApoE3 Protein", Hindawi Publishing Corporation, Cardiology Research and Practice, 2012, vol. 2012, Article ID 148796, 1-16 (17 pages).
Yuan-Ta Lin, et al., "APOE4 Causes Widespread Molecular and Cellular Alterations Associated with Alzheimer's Disease Phenotypes in Human iPSC-Derived Brain Cell Types", Neuron, 2018, vol. 98, 1141-1154 (24 pages).
Chantal Ferguson, "Targeting Apolipoprotein E With Tissue Specific Small Interfering RANS", Poster Presentations, Jul. 16, 2019, P950 (1 page).

(Continued)

*Primary Examiner* — Abigail Vanhorn
*Assistant Examiner* — Stephanie L Sullivan
(74) *Attorney, Agent, or Firm* — Sughrue Mion, PLLC

(57) ABSTRACT

The present invention relates to a trans-splicing ribozyme specific to Alzheimer's disease, and a use thereof. The trans-splicing ribozyme replaces RNA of genes that cause or increase the risk of Alzheimer's disease with RNA of genes that are beneficial for the treatment of the disease, thereby reducing the expression of the disease-causing genes and increasing the expression of the genes beneficial for the treatment of the disease, and thus can be usefully used to prevent or treat Alzheimer's disease.

14 Claims, 17 Drawing Sheets

Specification includes a Sequence Listing.

(56) References Cited

OTHER PUBLICATIONS

Chang Ho Lee, et al., "Therapeutic applications of group I intron-based trans-splicing ribozymes", WIREs RNA, 2018, vol. 9, e1466, 1-16 (16 pages).
Maria Elena Avale, et al., "Trans-splicing correction of tau isoform imbalance in a mouse model of tau mis-splicing", Human Molecular Genetics, 2013, vol. 22, No. 13, 2603-2611 (9 pages).
Lebedeva et al. "Phosphorothioate Oligodeoxynucleotides as Inhibitors of Gene Expression: Antisense and Non-Antisense Effects", Applications of Antisense Therapies to Restenosis, 1999, pp. 99-118 (20 pages total).
ALZFORUM Networking for a Cure, Mutations, APOE, Dec. 2024, (40 pages).
NCBI Reference Sequence: NM_001302690.2. Homo sapiens apolipoprotein E (APOE), transcript variant 4, mRNA, 2021 (5 pages).

* cited by examiner

TRANS-SPLICING RIBOZYME SPECIFIC TO APOE4 RNA AND USE THEREOF

CROSS REFERENCE TO RELATED APPLICATIONS

This application is a National Stage of International Application No. PCT/KR2021/002443 filed Feb. 26, 2021, claiming priority based on Korean Patent Application No. 10-2020-0025332 filed Feb. 28, 2020 and Korean Patent Application No. 10-2021-0025822 filed January Feb. 25, 2021.

SEQUENCE LISTING

The content of the electronically submitted sequence listing, file name: Q274237SUBSEQ05122026; size: 10,583 bytes; and date of creation: May 12, 2026, is incorporated herein by reference in its entirety.

TECHNICAL FIELD

The following description relates to a trans-splicing ribozyme specific to an APOE4 gene, and a use thereof.

BACKGROUND ART

People's life expectancy continues to increase as the economy develops, dietary life and sanitation conditions improve, and medical technology improves. In 2000, the proportion of the population aged 65 and overreached 7.2% in Korea, entering an aging society, and in 2017, the proportion exceeded 14%, becoming an aged society. As the proportion of the elderly over 65 years of age is rapidly increasing, the elderly population suffering from chronic geriatric diseases is increasing, which significantly reduces the quality of life of the elderly population and their families, and greatly increases social costs. Major geriatric diseases include dementia, Parkinson's disease, and stroke, and according to data from the National Health Insurance Corporation, between 2014 and 2018, 6,059,437 people were treated for dementia, Parkinson's disease, and stroke.

Alzheimer's disease is one of the main causes of dementia and is a degenerative brain disease in which abnormal proteins such as amyloid beta protein and tau protein accumulate in the brain and gradually damage brain neurons. Memory as well as cognitive functions gradually decline, and as it progresses further, speech and gait disorders appear, and thus the daily life becomes difficult alone.

Studies on the pathogenesis of Alzheimer's disease is mostly based on the amyloid hypothesis, and based thereon, studies on the amyloid precursor protein (APP), β-site amyloid precursor protein cleaving enzyme (BACE), and presenilin gene, studies on the interaction and regulation with other factors in cells, and studies on the generation, degradation and signal transduction of factors have been mainly conducted.

Due to the amyloid hypothesis, most therapeutic candidates on Alzheimer's disease are focused on 'inhibiting BACE1' and 'inhibiting the formation of amyloid beta fibrils.' However, Lilly's Solanezumab, an antibody targeting amyloid beta, failed in phase 3 clinical trials in patients with mild dementia, and the BACE1 inhibitor 'CNP520,' which Novartis and Amgen were jointly developing as an indication for Alzheimer's disease, also failed to improve the patient's cognitive function. Accordingly, the amyloid hypothesis, which was thought to be the cause of Alzheimer's disease, is being shaken, and there is an argument that the target molecule or the approach needs to be changed for the treatment of Alzheimer's disease.

ApoE (Apolipoprotein E) is a protein expressed in the liver and brain, and a number of research results supporting the relationship between ApoE protein expressed in the brain and Alzheimer's disease have been recently presented. It is known that ApoE protein has bimorphisms of ApoE2, ApoE3, and ApoE4, ApoE2 functions to protect neurons, and ApoE4 contributes to the accumulation of β-amyloid and exhibits neurotoxicity by itself. In addition, as a result of statistical analysis based on the metagenome study, it was found that APOE4 is a genetic factor that causes Alzheimer's disease. Therefore, an attempt to block the function of ApoE4 for the treatment of Alzheimer's disease is in progress, but the situation is still insufficient. On the other hand, the ApoE3 christchurch (ApoE3ch) mutation is a mutated version of ApoE3 found in elderly people in their 70s, and it has been found that amyloid plaques are found throughout the brain in people with this mutation. However, it has been revealed that cognitive impairment does not occur (Nature medicine 2019; 11:1680-1683.).

On the other hand, it has been reported that a group I intron ribozyme from *Tetrahymena thermophila* targets and then attaches an exon RNA attached to the 3' end of the ribozyme trans to the 5' exon in vitro, and thus a trans-splicing reaction that may link with separate transcripts may occur. This suggests that the trans-splicing reaction of group I ribozymes may also correct the transcript of genes related to several genetic diseases. Recently, it has actually been revealed that the β-globin gene transcript may be converted into an anti-sickling and γ-globin gene transcript by a trans-splicing ribozyme in erythrocyte precursor cells of patients with sickle cell disease.

As a gene therapy method, trans-splicing ribozyme may correct mutant gene RNA to normal RNA, and in the same principle, it may reduce the expression of a specific gene and simultaneously express a target gene in a host cell. In this case, since the ribozyme operates at the RNA level, there is an advantage in that it does not cause undesirable immune response problems and safety problems due to incorporation of genes at random locations in the host cell genome.

Accordingly, the present inventors conducted extensive research on a method for treating Alzheimer's disease using a trans-splicing ribozyme targeting APOE4, and then completed the present invention.

DISCLOSURE OF THE INVENTION

Technical Goals

The present invention is directed to addressing an issue associated with the related art, and to providing an Alzheimer's disease-specific trans-splicing ribozyme having excellent safety and expression efficiency and a use for treating Alzheimer's disease using the same.

However, the technical tasks to be achieved by the present invention are not limited to the aforementioned tasks, and other technical tasks, which are not mentioned herein, will be clearly understood from the following description by those having ordinary skill in the pertinent technical field.

Technical Solutions

The present invention provides a trans-splicing ribozyme that targets APOE4 RNA.

In one embodiment of the present invention, the trans-splicing ribozyme may have a structure of 5'-IGS (internal guide sequence)-Ribozyme*-exon-3'.

In another embodiment of the present invention, the IGS region may consist of a nucleotide sequence of 5 to 10 nt in length that may specifically bind to the 5' UTR region of APOE4 RNA and form a G/U wobble base pair, and may preferably consist of a nucleotide sequence of 5 to 10 nt in length that may form a G/U wobble base pair and complementarily bind to a region containing positions +21, +30, +33, +49, +56, +71, +77, +80, +82, +95, +98, +104, +128, +140, +181, +229, +255, +263, +275, +326, +368, +830, or a position +839, preferably, positions +21, +30, or +56 of APOE4 RNA.

In yet another embodiment of the present invention, the IGS region may include or consist of a nucleotide sequence represented by SEQ ID NO: 2, 4, or 6.

In yet another embodiment of the present invention, the trans-splicing ribozyme may further include an antisense sequence (AS) region capable of complementary binding to a portion of the APOE4 gene upstream of an IGS region.

In yet another embodiment of the present invention, the length of the AS region may be 10 nt to 200 nt, preferably 50 nt to 150 nt.

In yet another embodiment of the present invention, the trans-splicing ribozyme may include an IGS region consisting of SEQ ID NO: 2 and an AS region having a length of 150 nt.

In yet another embodiment of the present invention, the trans-splicing ribozyme may include an IGS region consisting of SEQ ID NO: 4 and an AS region having a length of 50 nt.

In yet another embodiment of the present invention, 5 to 10 random nucleotides may be included between the IGS region and the AS region, in which the random nucleotide sequence may be a restriction enzyme sequence, and the random nucleotide sequence may preferably be 6 nt in length and may consist of a sequence complementary to a portion of P1 and P10 illustrated in FIG. 10.

In yet another embodiment of the present invention, the Ribozyme* region may include or consist of the nucleotide sequence represented by SEQ ID NO: 7.

In yet another embodiment of the present invention, the exon region may be a gene for preventing or treating Alzheimer's disease and may include a part or all of a nucleotide sequence encoding ApoE2 or ApoE3 christchurch mutation (R136S).

In addition, the present invention provides a trans-splicing ribozyme expression vector containing the nucleotide sequence of the trans-splicing ribozyme and/or a nucleotide sequence complementary thereto.

In one embodiment of the present invention, the expression vector may further include a promoter operably linked to the ribozyme gene, in which the promoter may be a neuron-specific promoter, and the nerve cell includes neurons, astrocytes, and oligodendrocytes.

In addition, the present invention provides a gene delivery system including the trans-splicing ribozyme expression vector.

In addition, the present invention provides a pharmaceutical composition for preventing or treating Alzheimer's disease including any one or more selected from the group consisting of the trans-splicing ribozyme, a vector capable of expressing the same, and a gene delivery system containing the vector as an active ingredient.

In addition, the present invention provides a method for preventing or treating Alzheimer's disease including administering to a subject any one or more selected from the group consisting of the trans-splicing ribozyme, a vector capable of expressing the same, and a gene delivery system containing the vector.

In one embodiment of the present invention, the subject may be a human in need of prevention or treatment of Alzheimer's disease, more specifically, an Alzheimer's disease patient, an elderly person (over 60 years old), or an APOE4 allele carrier.

In another embodiment of the present invention, the method may further include measuring a degree of cognitive ability of a subject.

In addition, the present invention provides a use of the trans-splicing ribozyme, a vector capable of expressing the same, or a gene delivery system containing the vector for the production of a medicament for preventing or treating Alzheimer's disease. In the present invention, the Alzheimer's disease is a neurodegenerative disease in which brain nerve cells are gradually damaged as abnormal proteins such as amyloid beta protein and tau protein accumulate in the brain, and includes other diseases appearing as Alzheimer's disease progresses, for example, diseases such as Alzheimer's dementia.

Effects

The trans-splicing ribozyme according to the present invention replaces RNA of genes that cause or increase the risk of Alzheimer's disease with RNA of genes that are beneficial for the treatment of the disease, thereby reducing the expression of the genes that cause or increase the risk of the disease and increasing the expression of the genes beneficial for the treatment of the disease specifically in a cell or tissue expressing the target gene, and thus can be usefully used to prevent or treat Alzheimer's disease.

BRIEF DESCRIPTION OF DRAWINGS

FIG. 5A is a diagram identified at the protein level. FIG. 5B is a diagram identified at the gene level. FIG. 5C is a sequencing result of the trans-splicing product (SEQ ID NO: 26).

FIG. 9A is a diagram identified at the protein level. FIG. 9B is a diagram identified at the gene level. FIG. 9C is a sequencing result of a trans-splicing product (SEQ ID NO: 27).

FIG. 10A illustrates the structure of the +21 targeting ribozyme (SEQ ID NO: 28; SEQ ID NO: 29; SEQ ID NO: 30). FIG. 10B illustrates the structure of the +30 targeting ribozyme (SEQ ID NO: 31; SEQ ID NO: 32; SEQ ID NO: 33). FIG. 10C illustrates the structure of the +56 targeting ribozyme (SEQ ID NO: 34; SEQ ID NO: 35; SEQ ID NO: 36). Upstream of the IGS region of each ribozyme may include three nucleotide regions (P1) complementary to APOE4 RNA to increase the binding specificity and binding force of the ribozyme with the target. In addition, as illustrated in FIGS. 10A-10C, each ribozyme includes a P10 region with a length of 5-10 nt complementary to a 5' region including the P1 region at a position downstream of the Ribozyme* region, thereby increasing the trans-splicing efficiency of the ribozyme. With respect to a specific sequence of the ribozyme excluding the AS region and exon region, +21 targeting ribozyme may consist of or contains the nucleotide sequence represented by SEQ ID NO: 8, +30 targeting ribozyme represented by SEQ ID NO: 9, and +56 targeting ribozyme represented by SEQ ID NO: 10.

BEST MODE FOR CARRYING OUT THE INVENTION

Figure 1A:
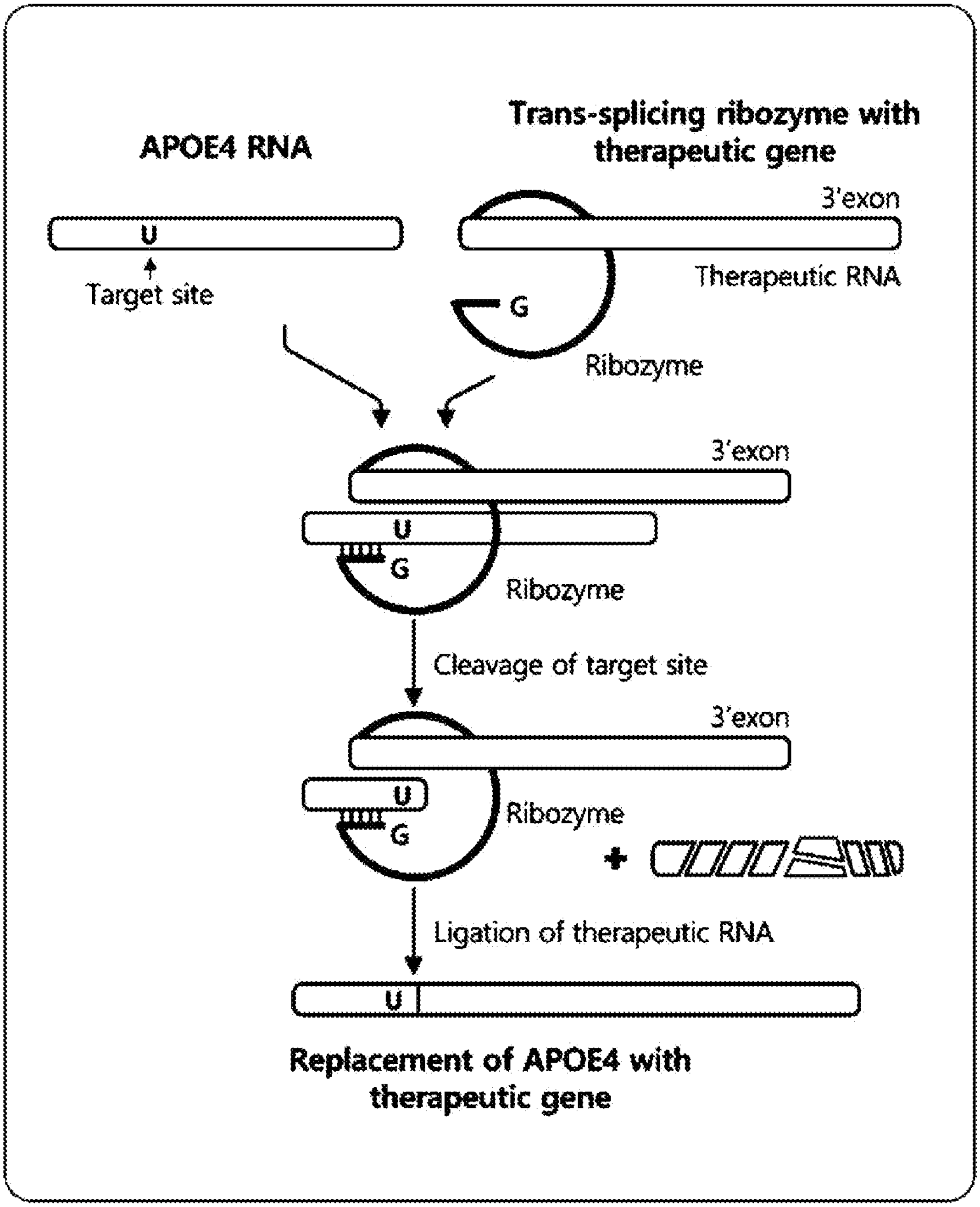
FIG. 1 is a schematic diagram of the mechanism of action of a trans-splicing ribozyme targeting APOE4 RNA (FIG. 1A), and a diagram of the result of comparing the sequences of ApoE RNA variants to construct a trans-splicing ribozyme for an ApoE4 RNA target (FIG. 1B).

The present inventors studied the cytotoxicity and β-amyloid accumulation function of the APOE4 protein itself and the gene therapeutic method for the prevention and treatment of Alzheimer's disease targeting APOE4 from the statistical results that there are many APOE4 allele carriers among Alzheimer's disease patients, and then completed a trans-splicing ribozyme targeting APOE4.

More specifically, the present inventors identified a common sequence in the 5'-UTR region through analyzing the sequence of various APOE RNA variants and set the region including a nucleotide at position +56 of APOE4 RNA as a target. To improve reaction specificity with APOE4 RNA, a trans-splicing ribozyme (+56 targeting ribozyme) including an internal guide sequence (IGS) complementary to the target region was designed (Example 1). It was identified that +56 targeting ribozyme was accurately trans-spliced at the desired position of APOE4 RNA (Examples 2 and 3).

Subsequently, the present inventors introduced an antisense (AS) region having a sequence complementary to APOE RNA at the 5' end of the ribozyme in order to increase the target specificity and trans-splicing efficiency of the +56 targeting ribozyme and introduced the luciferase gene into the 3' exon region to identify the degree of trans-splicing activity by measuring the luciferase activity. As a result, it was found that the introduction of the AS region and the length of the introduced AS region affected the trans-splicing efficiency of the ribozyme (Example 3-1).

As a result of performing the same experiment in a neuron-derived cell line for the design of a neuron-specific and more efficient trans-splicing ribozyme, it was understood that the +56 targeting ribozyme showed excellent trans-splicing efficiency when the 150 nt-long AS region was introduced (Example 3-2).

Subsequently, the present inventors identified the reaction site through sequencing of the trans-splicing product generated by mixing APOE4 RNA and random library ribozyme to secure a target region other than a nucleotide at position +56 of APOE4 RNA and identified the trans-splicing effect of the ribozyme targeting each reaction site. As a result, it was understood that in addition to a nucleotide at position +56, +21, +30, +71, and +77 sites of APOE4 RNA could be used as effective target regions. In particular, it was identified that the trans-splicing efficiency of ribozymes targeting +21 and +30 of APOE4 RNA was excellent (Example 4).

In addition, as a result of investigating the optimal AS region length according to the change in the target position of APOE4 RNA, the present inventors identified that +21 targeting ribozyme increased trans-splicing efficiency when the 50 nt-long AS region was introduced (Example 5).

From the above results, the present inventors understood that in a ribozyme targeting APOE4 RNA, the target site preferably includes nucleotides at positions +21, +30, and +56, and by including an IGS sequence with a length of 5-10 nt complementary to the region, efficient trans-splicing might occur specifically for APOE4 RNA.

In addition, in a ribozyme targeting APOE4 RNA, when an AS region of a sequence complementary to APOE4 RNA is included in the upstream of the IGS region, it can be seen that trans-splicing efficiency may be increased, but the optimal length of the AS region for efficiency enhancement differs depending on the target site (target nucleotide) and the target cell.

The present inventors provide a trans-splicing ribozyme for reducing the expression of APOE4 protein particularly in neurons, for the prevention and treatment of Alzheimer's disease, and the ribozyme may have a 5'-IGS (internal guide sequence)-Ribozyme*-exon-3' or 5'-AS (antisense)-IGS-Ribozyme*-exon-3' structure.

The term "ribozyme" used herein is an RNA molecule acting as an enzyme or a protein molecule including the RNA molecule, and it is also called an RNA enzyme or catalytic RNA. The ribozyme is an RNA molecule having a three-dimensional structure, which performs a chemical reaction and has a catalytic or self-catalytic property. It is known that some ribozymes cleave themselves or other RNA molecules to inhibit activity and that other ribozymes catalyze the aminotransferase activity of a ribosome. Such ribozymes may include a hammerhead ribozyme, a VS ribozyme, a hairpin ribozyme, and the like.

The term "trans-splicing" used herein refers to linking RNAs derived from different genes to each other.

In the present specification, the ribozyme refers to a trans-splicing ribozyme that cleaves APOE4 RNA and replaces it with self-RNA (particularly, the 3' exon region of the ribozyme) to inhibit the expression of APOE4 protein in a host cell and induce the expression of a gene encoded in an exon region. In the present invention, the ribozyme may have a 5'-IGS (internal guide sequence)-Ribozyme*-exon-3' or 5'-AS (antisense)-IGS-Ribozyme*-exon-3' structure. Ribozyme* region in the structure refers to a region that performs the function of cleavage of APOE4 RNA and/or substitution with an exon region in the trans-splicing ribozyme and may include or consist of the nucleotide sequence represented by SEQ ID NO: 7. In the present specification, unless otherwise specified, ribozyme refers to a trans-splicing ribozyme including the entire structure including the Ribozyme* region, which is a substantially functional performance region.

In the present invention, the gene encoded in the 3' exon region of the ribozyme may be a gene encoding a known protein (or peptide) known to have neuroprotective activity, preferably an APOE2 or APOE3 christchurch gene.

The term "vector" used herein is an expression vector capable of expressing a trans-splicing ribozyme within suitable host cells and a gene construct including an essential regulatory element operably linked in order to express a gene insert included in the vector.

The term "operably linked" used herein refers to a functional linkage between a nucleic acid expression regulating sequence performing a general function and a nucleic acid sequence encoding a target gene.

For example, when a ribozyme-encoding sequence is operably linked to a promoter, the expression of the ribozyme-encoding sequence will be under the influence or control of the promoter. Two nucleic acid sequences (the ribozyme-encoding sequence and a promoter region sequence at the 5' end of the ribozyme-encoding sequence) are operably linked when promoter activity is induced and the ribozyme-encoding sequence is then transcribed, and it may be considered that the two nucleic acid sequences are operably linked when the linkage properties between the two sequences do not induce a frameshift mutation, and the expression regulating sequence does not inhibit ribozyme expression. The operable linkage to the recombinant vector may be formed using a gene recombination technique well known in the art, and site-specific DNA cleavage and linkage may use an enzyme generally known in the art.

The vector according to the present invention may include a signal sequence or leader sequence for membrane targeting or secretion as well as expression regulatory factors such as a promoter, an operator, an initiation codon, a termination codon, a polyadenylation signal, and an enhancer, and may be manufactured in various ways according to an intended purpose. A promoter of the vector may be a constitutive or inducible promoter. In addition, the expression vector may include a selectable marker for selecting host cells containing a vector, and in the case of a replicable expression vector, an origin of replication may be included. The vector may be self-replicated or integrated into host DNA.

The vector according to the present invention is preferably a plasmid vector, a cosmid vector or a virus vector, and most preferably, a virus vector. The virus vector is preferably derived from a retrovirus, such as human immunodeficiency virus (HIV), murine leukemia virus (MLV), avian sarcoma/leucosis virus (ASLV), spleen necrosis virus (SNV), Rous sarcoma virus (RSV) or mouse mammary tumor virus (MMTV), an adenovirus, an adeno-associated virus (AAV), or a herpes simplex virus (HSV), but the present invention is not limited thereto. The recombinant vector according to the present invention may most preferably be a recombinant adeno-associated viral vector.

The term "promoter" used herein is a part of DNA, which is involved in binding of an RNA polymerase in order to initiate transcription. Generally, the promoter is located adjacent to a target gene as well as at an upper region thereof, and as a site to which a transcription factor which is an RNA polymerase or a protein inducing an RNA polymerase binds, the enzyme or protein can be induced to be located at a proper transcription start region. That is, the promoter includes a specific gene sequence which is located at the 5' region of a gene to be transcribed in a sense strand and induces the initiation of mRNA synthesis for a target gene when an RNA polymerase binds to a corresponding site directly or via a transcription factor.

The promoter according to the present invention may be a neuron type-specific promoter from the viewpoint of increasing gene expression in neurons, and the nerve cells include neurons, astrocytes, and oligodendrocytes.

The term "gene delivery system" used herein refers to a system that can increase expression efficiency by increasing intracellular delivery efficiency for a ribozyme gene and/or nucleic acid sequence and may be classified into a virus-mediated system and a non-viral system.

The virus-mediated system uses a viral vector such as a retrovirus vector, an adenovirus vector, or an adeno-associated viral vector, and is known to have relatively higher intracellular gene delivery efficiency than a non-viral system since it uses a virus's inherent intercellular invasion mechanism that infects human cells. In addition, after entering cells, a non-viral vector has a drawback of gene degradations in an endolysosome after the endosome is fused with a lysosome, whereas a viral vector has an advantage of high gene delivery efficiency because of less gene loss thanks to a mechanism of delivering a gene into a nucleus without passing through a lysosome.

The viral vector that can be used in the present invention may be a vector derived from a retrovirus, an adenovirus or an adeno-associated virus as described in the disclosure on the recombinant vector. The viral vector may be introduced into cells by a transduction method, such as infection, after assembly into a viral particle.

The non-viral system is a method of using a cationic lipid delivery system or cationic polymer delivery system as a delivery vehicle for a nucleic acid and/or a gene, or a method of using electroporation.

A cationic lipid delivery system is a method of forming a complex using a positive charge of a nanometer-sized liposome mainly consisting of a cationic lipid or nanoparticles made of a lipid with a negatively charges gene, an expression vector or nucleic acid containing the gene, and then delivering the complex into cells by endocytosis. The complex delivered into cells is first delivered to a lysosome from an endosome, exported through the cytoplasm and then expressed. A cationic polymer delivery system delivers a gene in a manner similar to the cationic lipid delivery system, except that a polymer is used instead of a lipid, and representative cationic polymers include polyethyleneimine, poly-L-lysine and chitosan.

Accordingly, the recombinant vector of the present invention may be combined with a cationic lipid delivery system or cationic polymer delivery system, thereby forming a complex, and the resulting complex may be used as a gene delivery system.

In the present invention, the gene delivery system may include the above-described recombinant vector and may be one of a virus-mediated system and a non-viral system, and preferably, a virus-mediated system.

The trans-splicing ribozyme of the present invention may inhibit APOE4 protein expression by targeting APOE4 RNA in neurons, and APOE4 is known as a major risk-causing gene for Alzheimer's disease. Therefore, the trans-splicing ribozyme of the present invention, the ribozyme expression vector, and a gene delivery system containing the vector may be used in a pharmaceutical composition for preventing or treating Alzheimer's disease.

The term "prevention" used herein refers to all actions of inhibiting Alzheimer's disease or delaying the onset thereof by administration of a pharmaceutical composition according to the present invention.

The term "treatment" used herein refers to all actions involved in alleviating or beneficially changing symptoms of Alzheimer's disease by administration of the composition containing the vector according to the present invention.

The pharmaceutical composition according to the present invention may further include a pharmaceutically acceptable carrier, excipient, or diluent. Examples of a pharmaceutically acceptable carrier, excipient or diluent that can be used in the pharmaceutical composition according to the present invention may include lactose, dextrose, sucrose, sorbitol, mannitol, xylitol, erythritol, maltitol, starch, acacia gum, alginate, gelatin, calcium phosphate, calcium silicate, calcium carbonate, cellulose, methyl cellulose, polyvinylpyrrolidone, water, methylhydroxy benzoate, propylhydroxy benzoate, talc, magnesium stearate, mineral oil, and the like.

The pharmaceutical composition of the present invention may be administered orally or parenterally, and preferably, parenterally according to a desired method.

According to one embodiment of the present invention, the pharmaceutical composition according to the present invention may be administered intravenously, intraarterially, intracerebrally, subcutaneously, or intracisternal injection. The injection according to the present invention may be dispersed in a sterilized medium to be used without modification when being administered to a patient and may be administered after being dispersed at a suitable concentration using distilled water for injections. In addition, when the pharmaceutical composition is prepared as an injection, it may be mixed with a buffer, a preservative, an analgesic, a solubilizer, an isotonic agent, a stabilizer, or the like to be formed in a unit dose ampoule or multiple-dose form.

The dose of the pharmaceutical composition of the present invention may vary depending on the condition and body weight of a patient, the severity of a disease, a drug type, an administration route, and time, and may be suitably selected by one of ordinary skill in the art. The pharmaceutical composition according to the present invention may be used alone, or in combination with other Alzheimer's drugs or therapeutic methods.

In the present invention, when a certain portion "comprises or includes" a certain component, this indicates that other components may be further included, rather than excluding other components, unless otherwise stated.

MODE(S) FOR CARRYING OUT THE INVENTION

Hereinafter, embodiments will be given to describe the present specification in detail. However, the embodiments according to the present specification may be modified in various other forms, and the scope of the present specification is not to be construed as being limited to the embodiments described below. The embodiments of the present specification are provided to more completely explain the present specification to those having ordinary skill in the pertinent field.

Figure 1B:
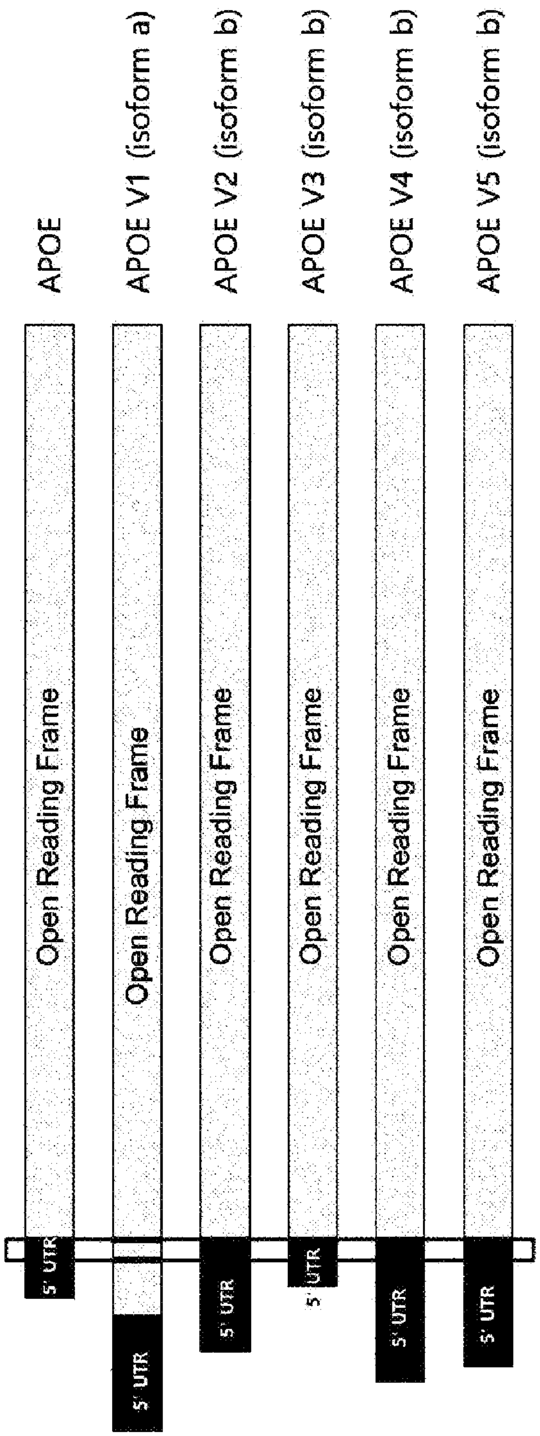

Example 1. ApoE4 RNA+56 Targeting Trans-Splicing Ribozyme Design and Preparation Thereof In order to select a target RNA site, the sequences of APOE RNA variants (V1 to V5) published in NCBI were compared. Among the common sequence (23 bp) of 5'-UTR, a sequence containing uracil (U) base capable of forming a ribozyme and G-U wobble base pair (GCCAAU: SEQ ID NO: 1) was selected as the target site (FIG. 1).

Figure 2:
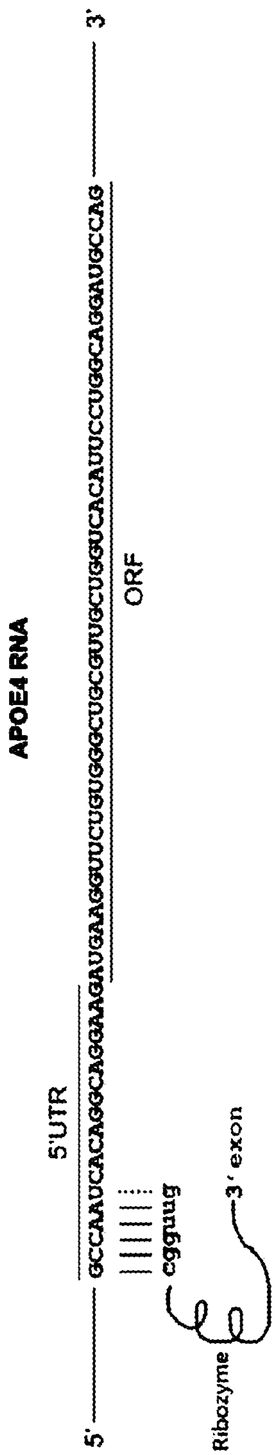
FIG. 2 is a diagram schematically showing the trans-splicing ribozyme for an ApoE4 RNA target of the present invention (SEQ ID NO: 21 and (SEQ ID NO: 22).

The target site includes the base at position +56 of APOE4 RNA, and IGS (GUUGGC: SEQ ID NO: 2) capable of targeting the target site at the 5' end and a trans-splicing ribozyme targeting ApoE4 RNA into which ApoE2, the target gene to be substituted, is introduced at the 3' end (hereinafter, referred to as '+56 targeting ribozyme') were prepared (FIG. 2).

The +56 targeting ribozyme was cloned into a pcDNA vector to prepare a vector for trans-splicing ribozyme expression.

Example 2. Identification of Trans-Splicing Effect of +56 Targeting Ribozyme The effect of +56 targeting ribozyme prepared in Example 1 above was identified as follows.

After mixing 1 pmole of ribozyme and 1 pmole of ApoE4 RNA with trans-splicing reaction buffer (50 mM HEPES, 150 mM NaCl, 5 mM $MgCl_2$, pH 7.0), the volume was adjusted to 9 μl, and heated at 95° C. for 1 minute. After standing at 37° C. for 3 minutes, 1 μl of 1 mM GTP was added to adjust the volume to 10 μl, and reacted at 37° C. for 3 hours. The RNA product after the reaction was recovered by phenol extraction/ethanol precipitation method and dissolved in 10 μl of distilled water (D.W) treated with DEPC (diethyl pyrocarbonate). 10 pmole of RY-RT primer (5'-ATGTGCTGCAAGGCGATT-3'; SEQ ID NO. 12) was added to the recovered RNA, heated at 95° C. for 1 minute, and left at room temperature for 10 minutes. Then, 1 μl of 10 mM dNTP, 4 μl of 5× RTase buffer, 1 μl of RTase and DEPC-treated D.W were added to the RNA to adjust the volume to 20 μl and reacted at 42° C. for 50 minutes to synthesize cDNA.

2 μl of synthesized cDNA, 10 μl of 5X PCR buffer, 1 μl of 10 mM dNTP, 10 pmole of ApoE4 forward primer (5'-CTACTCAGCCCCAGCGGAGGTGAAGG-3'; SEQ ID NO. 13), 10 pmole of RY-TS primer (5'-TGTAAAACGACGGCCAGTG-3'; SEQ ID NO. 14) and 0.2 μl of Phusion DNA taq polymerase were mixed. D.W was added thereto to adjust the volume to 50 μl, and the trans-splicing product DNA was obtained by amplifying 30 cycles under the conditions of 30 seconds at 98° C., 30 seconds at 55° C., and 15 seconds at 72° C. 5 μl of the PCR product was electrophoresed on a 2% TBE agarose gel to determine whether a trans-splicing product was prepared, and sequencing of the product was performed.

Figure 3:
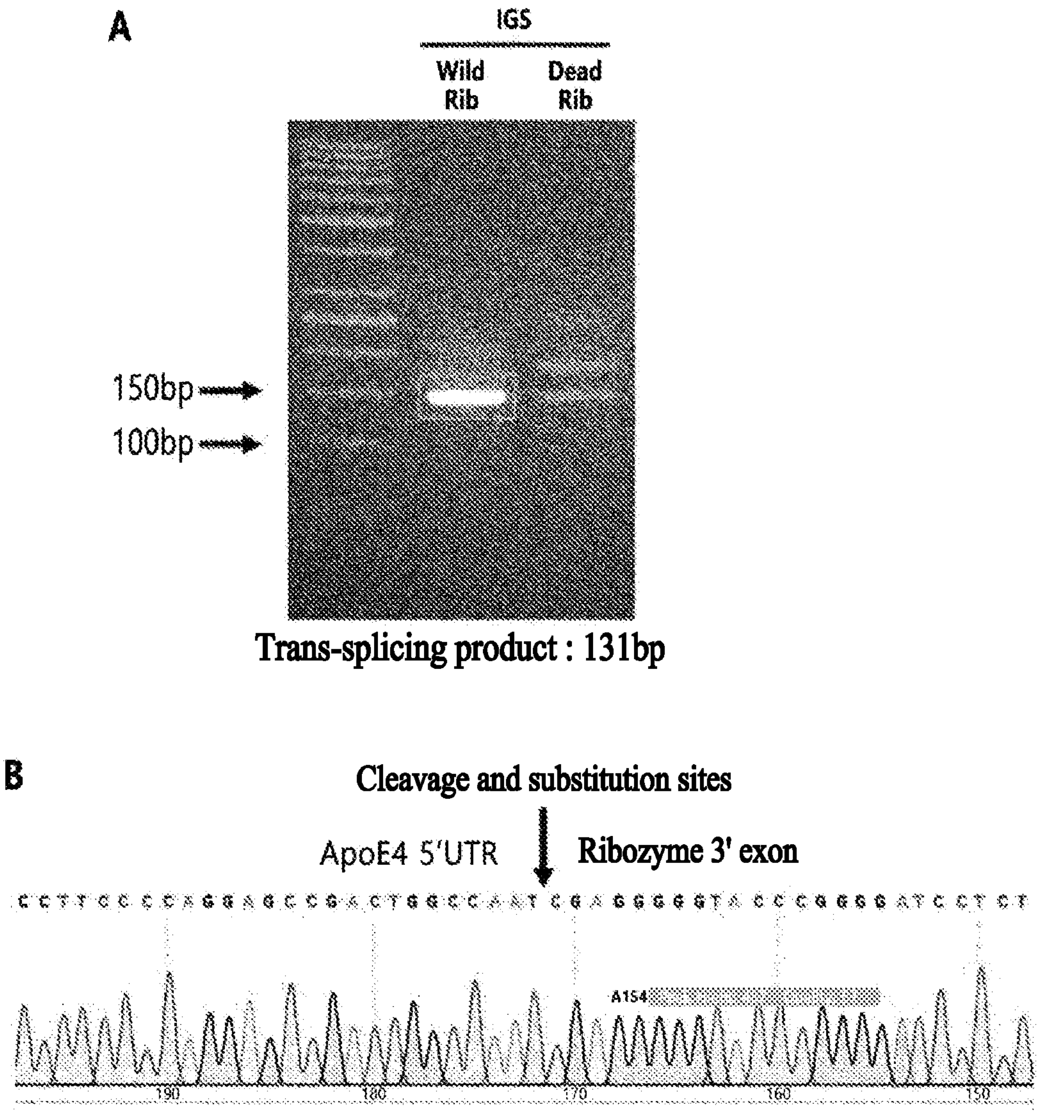
FIG. 3 identifies the trans-splicing effect of +56 targeting ribozyme targeting the +56$^{th}$ base of APOE4 RNA, where A is the result of identifying the production of a trans-splicing product by +56 targeting ribozyme, and B is the result of sequencing of the prepared trans-splicing product (SEQ ID NO: 23).

As a result of electrophoresis, the trans-splicing product (131 bp) generated when ApoE4 RNA was substituted with the 3' exon RNA of ribozyme could be identified, and as a result of sequencing, it was found that the product was the 3' exon RNA of the ribozyme linked to the 5'-UTR of ApoE4 RNA (FIG. 3).

Example 3. +56 Targeting Trans-Splicing Ribozyme Optimization 3-1. Identification of Effect of Introduction of Anti-Sense (AS) Region In order to increase target specificity and trans-splicing efficiency of the +56 targeting ribozyme prepared in Example 1, an antisense (AS) region having a sequence complementary to APOE4 RNA was introduced at the 5' end of the ribozyme. A luciferase gene was introduced into the 3' exon region of the ribozyme in order to identify the trans-splicing efficiency according to the length of the AS region. Luciferase activity was measured when the length of the AS region was 0 nt, 50 nt, 100 nt, or 150 nt.

Figure 4:
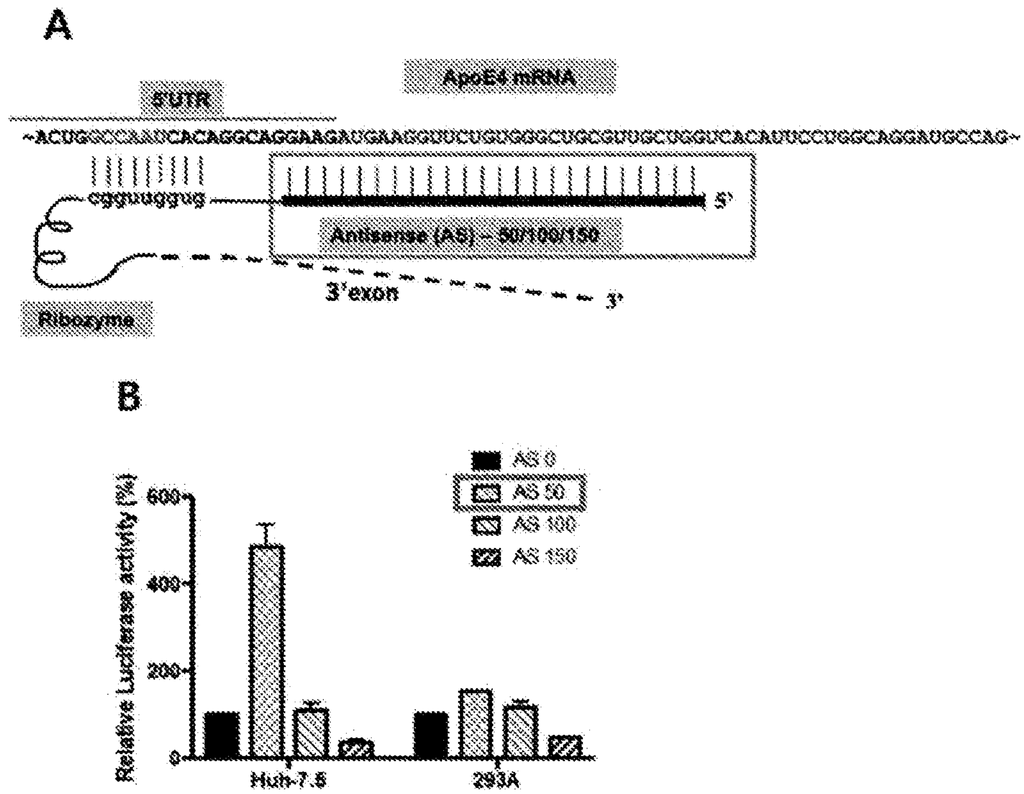
FIG. 4 identifies the effect of the AS region on trans-splicing efficiency, where A shows a structure in which an AS region is introduced at the 5' end of the trans-splicing ribozyme for an ApoE RNA target (SEQ ID NO: 24), and B is a graph identifying the trans-splicing efficiency of the ribozyme according to the introduction of the AS region and the length of the introduced AS region (SEQ ID NO: 25).

More specifically, each ribozyme expression vector was transfected into a Huh-7.5 cell line expressing ApoE and a 293A cell line not expressing the ApoE, and a luciferase assay was performed. As a result of identifying the luciferase signal, it was identified that in the Huh-7.5 cell line, the trans-splicing efficiency of the trans-splicing ribozyme introduced with 50 antisense sequences was remarkably excellent, but in the 293A cell line, there was no significant difference in the trans-splicing efficiency of each ribozyme (FIG. 4B).

From the above results, it was identified that the introduction of the AS region and the length of the AS region affected the trans-splicing efficiency of the ribozyme.

3-2. Optimization of AS Region Length According to Target Cell Line

As a target for prevention and treatment of Alzheimer's disease, the trans-splicing ribozyme should be able to be effectively trans-spliced in neurons to reduce APOE4 gene expression. Accordingly, the experiment of Example 3-1 above was repeated in a neuron-derived cell line, and the trans-splicing efficiency according to the length of the AS region was identified.

More specifically, $1\times10^5$ CCF-STTG1 (E3/E4, astrocyte) cells were cultured in a 12 well plate for 24 hours, and 500 ng of a plasmid vector expressing a +56 targeting ribozyme containing an AS region of different lengths (0 nt, 50 nt, 100 nt, or 150 nt) and 50 ng of a pTK-renilla luciferase plasmid vector were co-transfected for 48 hours. Then, after removing all of the culture medium, it was washed once with 500 μl of 1xPBS, and 100 μl of passive lysis buffer (Promega, E1980, Dual-Luciferase Reporter Assay System) was put into each well, and the cells were lysed by shaking at room temperature for 15 minutes. After recovering the lysate and centrifuging at 13000 rpm for 1 minute, 10 μl of the supernatant was taken and luciferase activity was measured (Promega, E1980, Dual-Luciferase Reporter Assay System). As a positive control (CF), CMV promoter-Firefly luciferase was used.

Figure 5A:
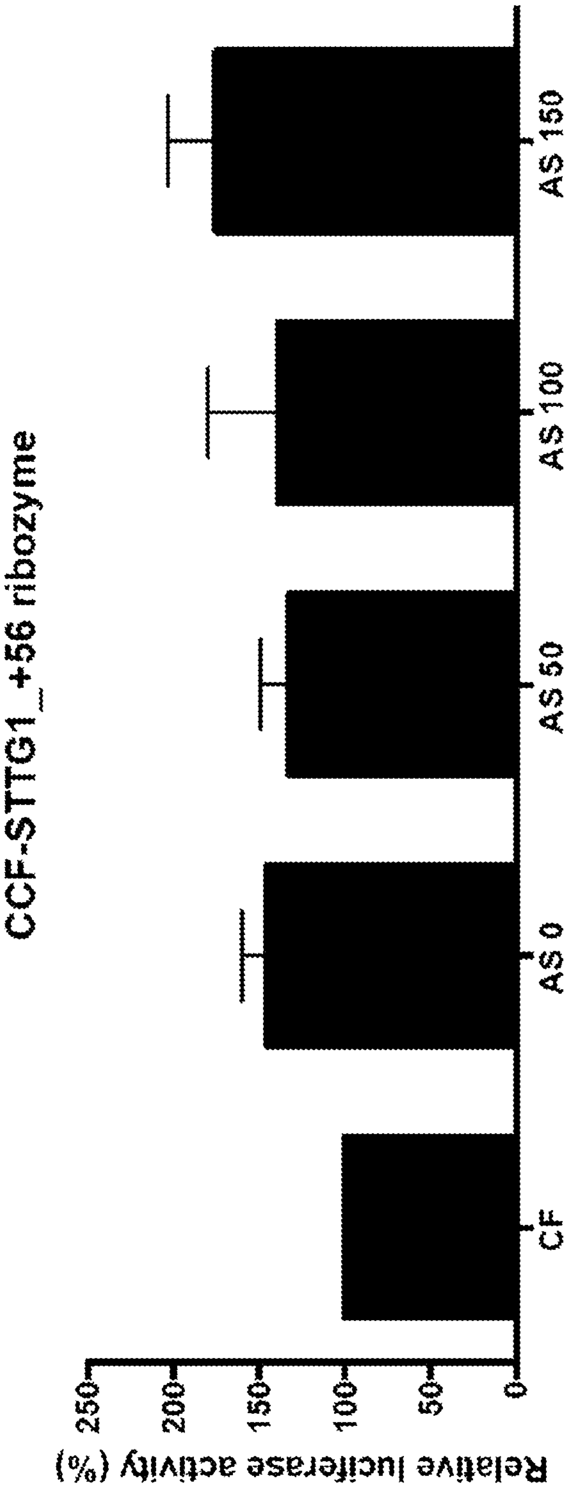
FIGS. 5A-5C identify the +56 targeting ribozyme trans-splicing efficiency according to the introduction of the AS region and the length of the introduced AS region in a neuron-derived cell line.

As a result, it was identified that trans-splicing of APOE4 RNA was induced by ribozyme in CCF-STTG1 cells regardless of the introduction of the AS region and the length of the AS region. In particular, it was identified that the trans-splicing efficiency by the ribozyme including the AS region of 150 nt-length was excellent (FIG. 5A).

Figure 5B:
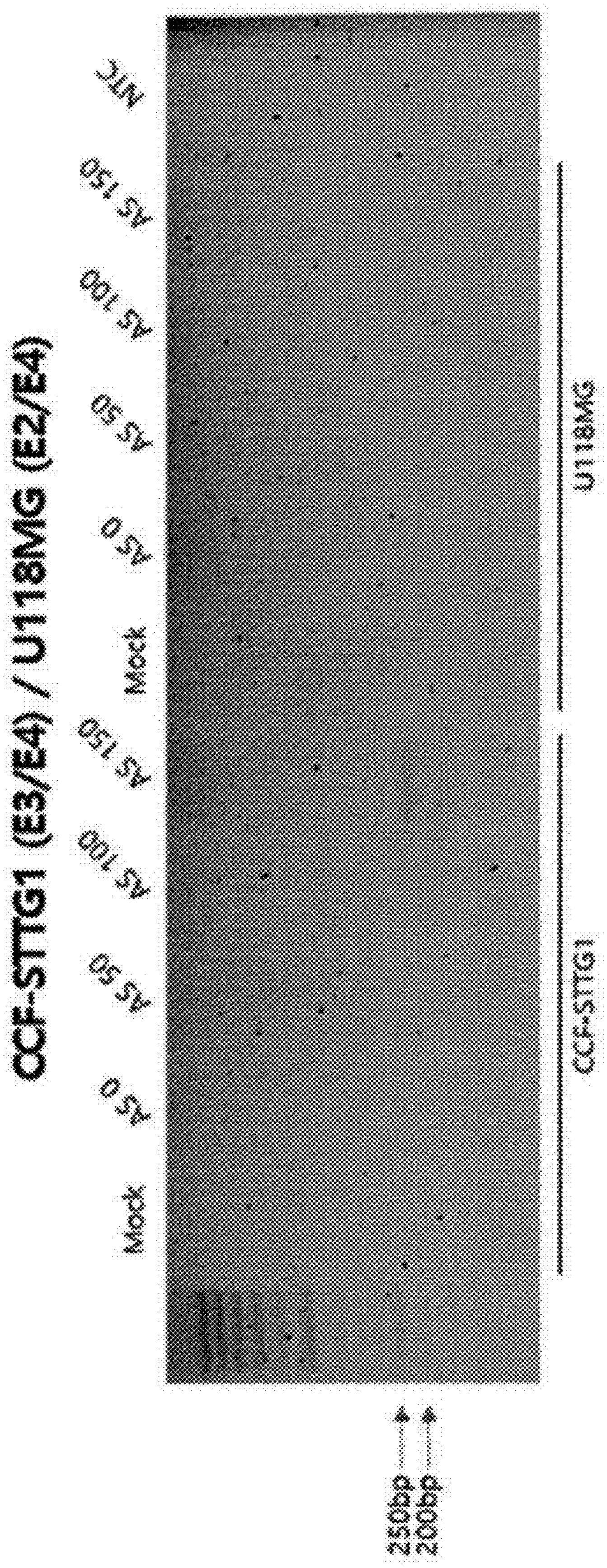

In order to re-verify the results at the gene level, electrophoresis was performed to detect a trans-splicing product. More specifically, $2\times10^5$ CCF-STTG1 or U118MG (E2/E4) cells were cultured in a 6 well plate for 24 hours, and transformation was induced with 2.5 μg of +56 targeting ribozyme expression vector. After 48 hours, all of the culture medium was removed, washed once with 1 mL of 1xPBS, and the cells recovered and 100 μL of chloroform were mixed to extract total RNA. After adding RT primer (5'-CCCATATCGTTTCATAGCTTCTGCC-3'; SEQ ID NO. 15) to 1 μg of the extracted total RNA, reverse transcription was performed under 20 μL volume conditions to generate cDNA. 2 μL of the cDNA was mixed with a forward primer (5'-CAGCGGAGGTGAAGGACGT-3'; SEQ ID NO. 16) and a reverse primer (5'-ATGTTCACCTCGATATGTG-CATC-3'; SEQ ID NO. 17) and subjected to 30 cycle PCR under the conditions of 30 seconds at 95° C., 30 seconds at 58° C., and 30 seconds at 72° C., and the PCR band was identified on 2% TBE agarose gel. As a result, it was possible to identify the 211 bp PCR DNA band expected as a trans-splicing product, and in particular, the darkest band was identified in the cells transformed with the ribozyme including the 150 nt-long AS region (FIG. 5B).

Figure 5C:
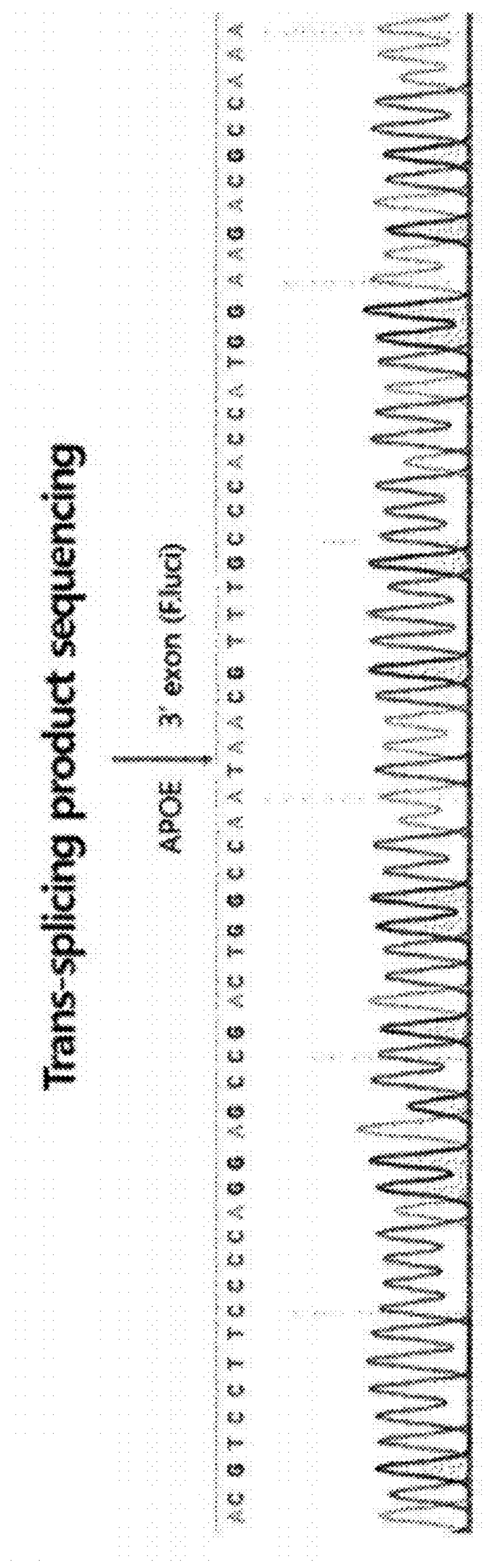
Figure 6:
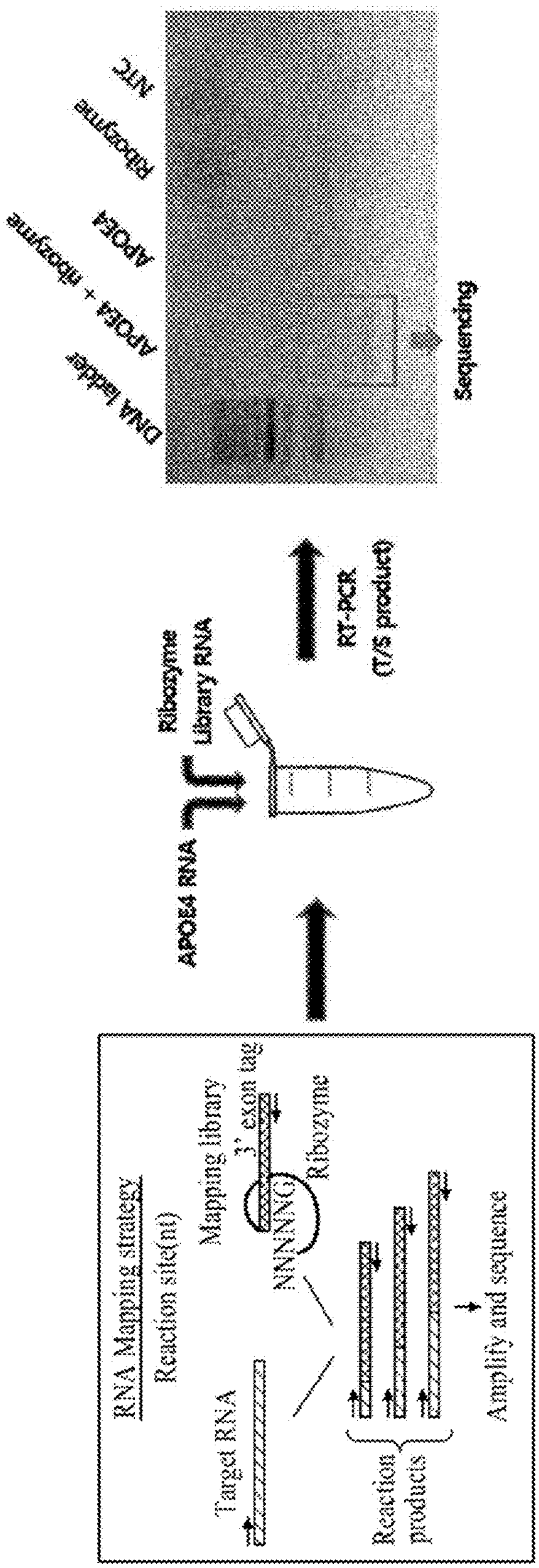
FIG. 6 is a schematic diagram and a result of a reaction site mapping experiment of APOE4 RNA in vitro.

Subsequently, as a result of performing the 211 bp PCR DNA sequencing to identify that trans-splicing was performed at the desired position, it was identified that trans-splicing occurred precisely at the expected trans-splicing site, and APOE RNA+reporter RNA (Firefly luciferase) fusion RNA was generated (FIG. 5C).

Example 4. IGS Region Optimization 4-1. In Vitro Mapping

In order to secure various tools for APOE4 protein removal from neurons, after mixing and reacting APOE4 RNA with random library ribozyme in a test tube, RT-PCR was performed, and then, the APOE4 RNA site where trans-splicing occurred was identified through sequencing of the PCR DNA band expected to be a trans-splicing product.

More specifically, APOE4 RNA was synthesized through the in-vitro transcription process, and a trans-splicing ribozyme RNA library having a random sequence (GNNNNN; (SEQ ID NO: 18) at the 5' end was synthesized through the in vitro transcription process. 0.1 pmole of APOE4 RNA and 1 pmole of ribozyme library RNA were mixed with 1 X in vitro trans-splicing reaction buffer (50 mM Hepes (pH 7.0), 150 mM NaCl, 5 mM $MgCl_2$) to make a total of 9 μL, reacted at 95° C. for 1 minute and 37° C. for 3 minutes, 1 μL of 1 mM GTP was added, and the concentration was adjusted to final 0.1 mM GTP, followed by reaction at 37° C. for 3 hours. The reaction solution was subjected to phenol extraction/EtOH precipitation to recover RNA, and then RT-PCR was performed. Then, after adding ribozyme specific RT primer (5'-ATGTGCTGCAAGGC-GATT-3'; SEQ ID NO: 19), cDNA was synthesized by reverse transcription under 20 μL volume conditions. 2 μL of synthesized cDNA was used, 10 pmole of each of APOE4 RNA specific 5' primer (5'-CTACTCAGCCCCAGCG-GAGG-3'; SEQ ID NO: 13) and ribozyme specific 3' primer (RY-TS) (5'-TGTAAACGACGGCCAGTG-3'; SEQ ID NO: 20) was used, 35 cycle PCR was performed under the conditions of 30 seconds at 95° C., 30 seconds at 55° C., and 30 seconds at 72° C., and the PCR band was identified on 2% TBE agarose gel. After elution of all PCR bands identified through the gel extraction process, it was identified through nucleotide sequence analysis at which portion of the APOE4 RNA the trans-splicing reaction occurred. As a result, the reaction site and frequency of occurrence of trans-splicing in APOE4 RNA are shown in Table 1 below.

TABLE 1

| Reaction site | Number of clone |
|---|---|
| +21 | 19 |
| +30 | 3 |
| +70 | AUG initiation codon |
| +77 | 1 |
| +80 | 1 |
| +98 | 1 |
| +830 | 1 |
| +839 | 2 |

As shown in Table 1, it was identified that the most trans-splice occurred at the +21 site of APOE4 RNA. From the above results, it can be seen that a trans-splicing ribozyme targeting a nucleotide at position +21 of APOE4

RNA (hereinafter, +21 targeting ribozyme) is effective in reducing APOE4 protein expression.

4-2. Cell Mapping

Figure 7:
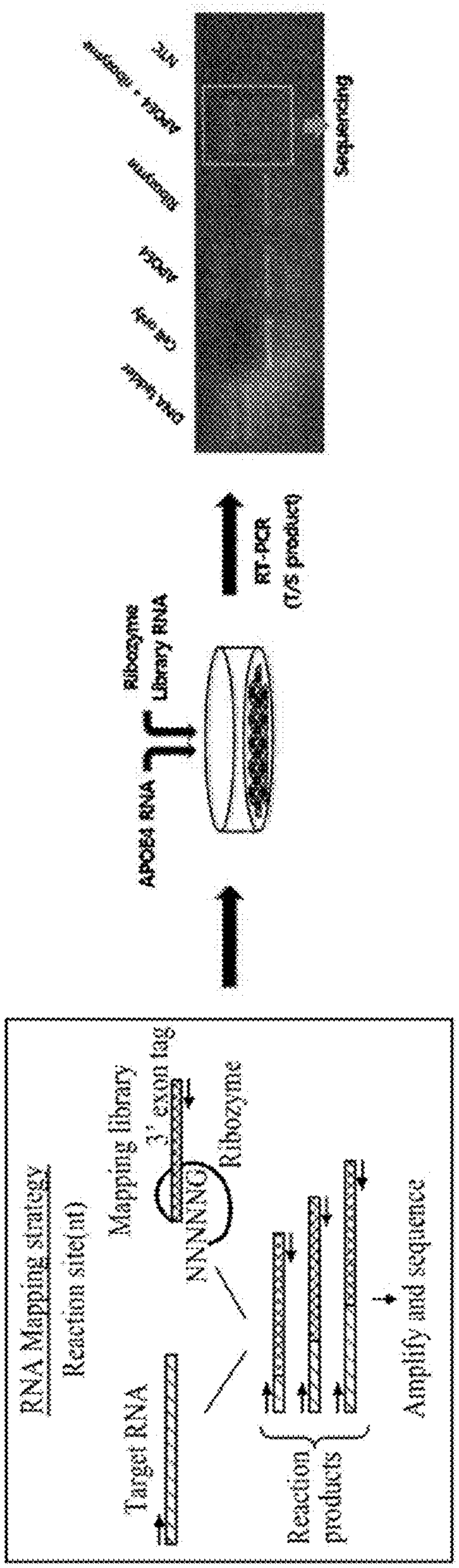
FIG. 7 is a schematic diagram and a result of a reaction site mapping experiment of APOE4 RNA in cells.

Following the trans splicing reaction site mapping result of APOE4 RNA on a test tube, the same experiment was performed in 293A cells by co-transfection of APOE4 RNA and random library ribozyme (FIG. 7). As a result, the reaction site and frequency of occurrence of trans-splicing in APOE4 RNA are shown in Table 2 below.

TABLE 2

| Reaction site (nt) | Number of clone |
|---|---|
| +30 | 1 → In vitro (3), total 4 |
| +33 | 1 |
| +49 | 1 |
| +71 | 3 |
| +77 | 2 → In vitro (1), total 3 |
| +80 | 3 → In vitro (1), total 4 |
| +82 | 4 |
| +95 | 1 |
| +104 | 1 |
| +128 | 2 |
| +140 | 2 |
| +181 | 1 |
| +229 | 2 |
| +255 | 2 |
| +263 | 1 |
| +275 | 1 |
| +326 | 2 |
| +368 | 1 |

4-3. Identification of Trans-Splicing Effect of Ribozyme Targeting Each Reaction Site Among the target sites identified through in vitro and cell mapping, +30, +71, +77, +80, and +82 sites identified as overlapping and a +21 site with the highest trans-splicing frequency for in vitro mapping were selected to prepare a ribozyme targeting each site, perform an in vitro trans-splicing reaction, and identify trans-splicing. +56 targeting ribozyme was used as a control group.

More specifically, 0.1 pmole of APOE4 RNA was mixed with 1 pmole of each trans-splicing ribozyme library RNA to induce a trans-splicing reaction. RNA was recovered from each reaction solution, RT-PCR was performed, and the prepared cDNA was amplified RNA PCR using APOE4 specific 5' primer (5'-CTACTCAGCCCCAGCGGAGG-3'; SEQ ID NO: 13), ribozyme specific 3' primer (5'-TGTAAAACGACGGCCAGTG-3'; SEQ ID NO: 14) (30 seconds at 95° C., 30 seconds at 55° C., 30 seconds at 72° C., 35 cycles), and each amplified product was identified by electrophoresis on agarose gel.

Figure 8:
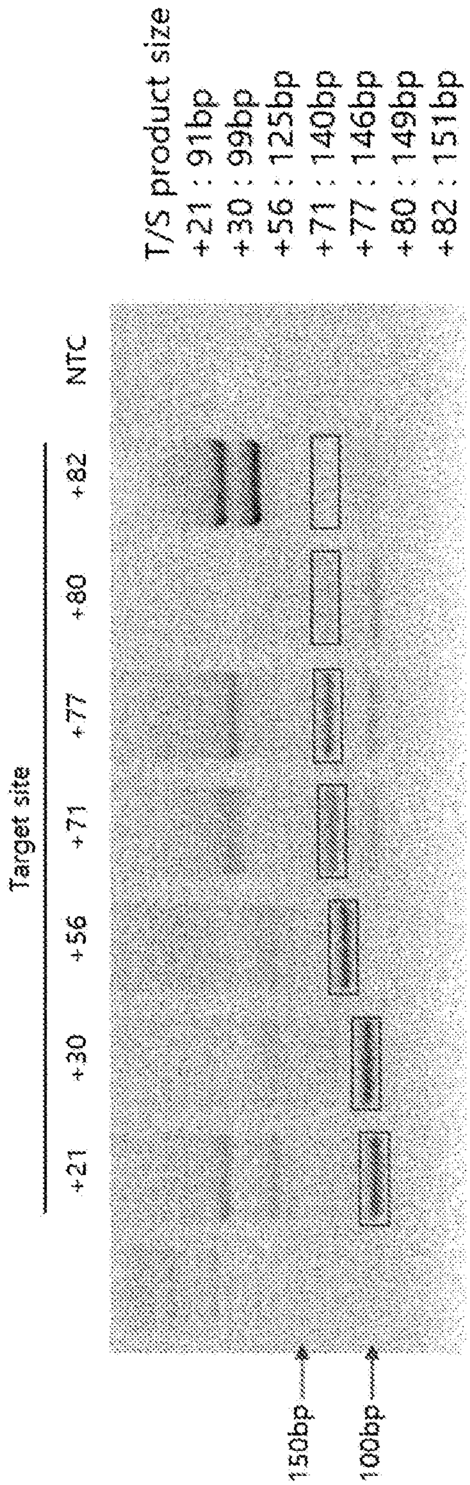
FIG. 8 is a diagram identifying the trans-splicing efficiency of ribozymes with different target positions of APOE4 RNA.

As a result, the trans-splicing efficiency by the ribozyme targeting the +21, +30, +71, and +77 sites of APOE4 RNA was excellent. In particular, it was identified that the efficiency of +21 targeting ribozyme and +30 targeting ribozyme was particularly excellent (FIG. 8).

In APOE4 RNA, the target region including a nucleotide at position +21 is 5'-GGAGGU-3' (SEQ ID NO: 3), and the IGS of the +21 targeting ribozyme has 5'-GCCUCC-3' (SEQ ID NO: 4). In addition, in APOE4 RNA, the target region including a nucleotide at position +30 is 5'-GGACGU-3' (SEQ ID NO: 5), and the IGS of +30 targeting ribozyme has 5'-GCGUCC-3' (SEQ ID NO: 6).

Example 5. +21 Targeting Trans-Splicing Ribozyme Optimization

Subsequently, in order to increase the target specificity and trans-splicing efficiency of the trans-splicing ribozyme with a different target site of APOE4 RNA, a ribozyme introduced with an AS region having a different length as in Example 3 was prepared. After transformation into Huh-7.5 cells, CCF-STTG1 cells, and U118MG cells, the degree of trans-splicing occurrence was identified at the protein level and the gene level.

Figure 9A:
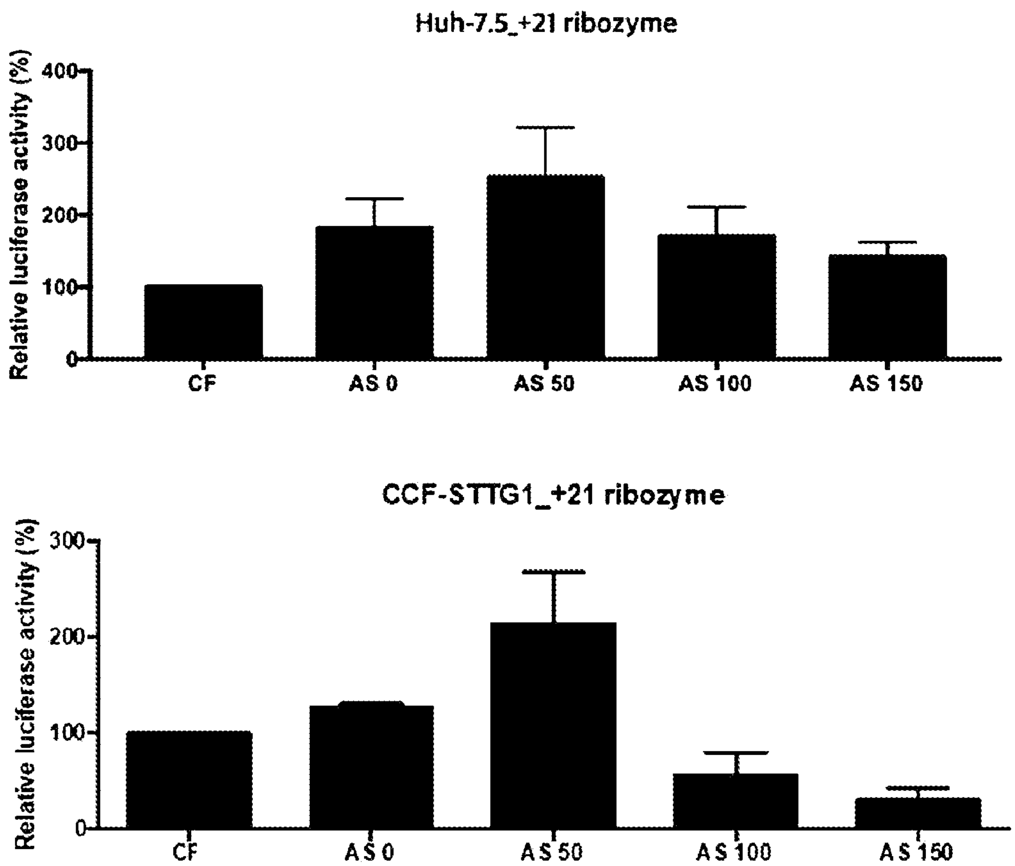
FIGS. 9A-9C identify the +21 targeting ribozyme trans-splicing efficiency according to the introduction of the AS region and the length of the introduced AS region.

As a result of identification at the protein level, the ribozyme targeting a nucleotide at position +21 of APOE4 RNA induced trans-splicing of APOE4 RNA in cells expressing APOE4 regardless of the introduction of the AS region and the length of the AS region. In particular, it was identified that the trans-splicing efficiency was remarkably excellent in the ribozyme introduced with a 50 nt-long AS region (FIG. 9A).

Figure 9B:
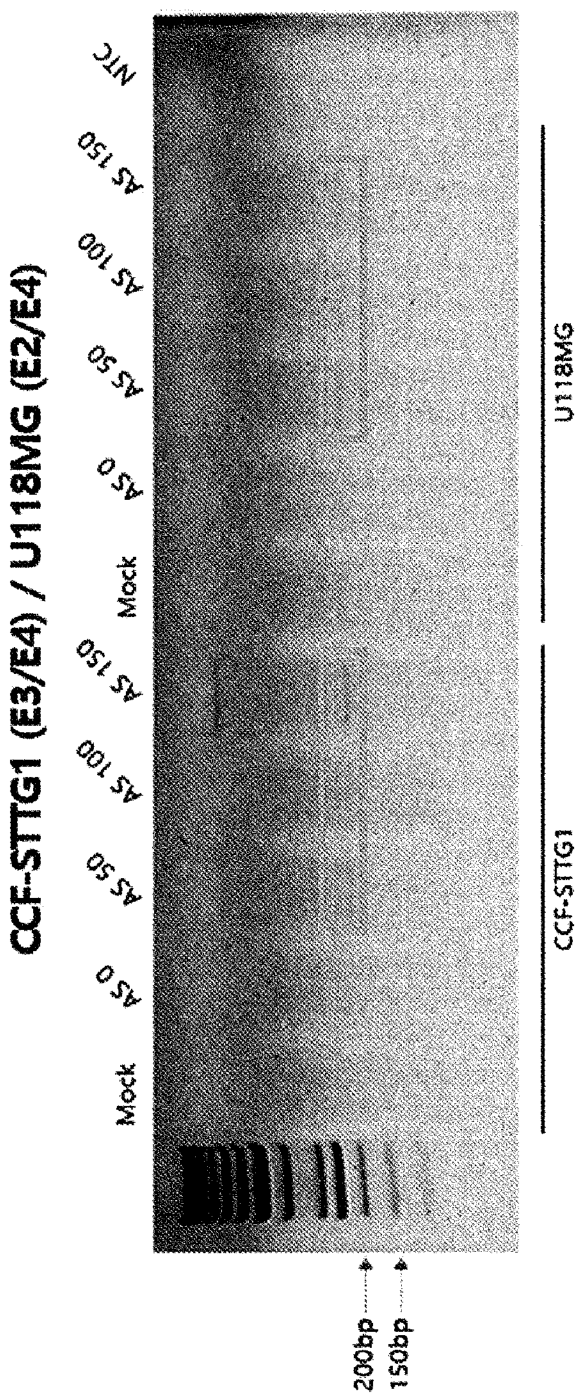
Figure 9C:
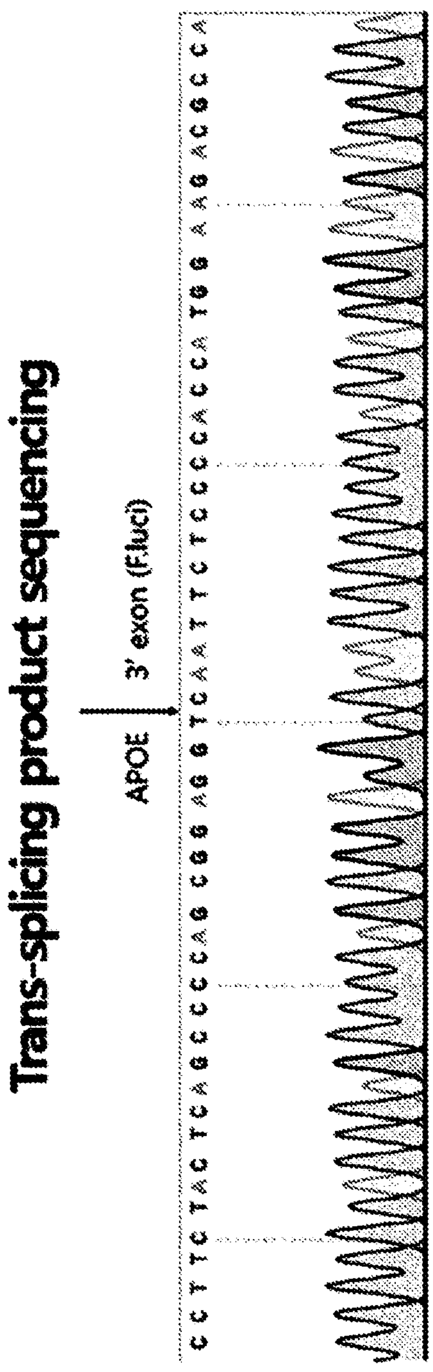
Figure 10A:
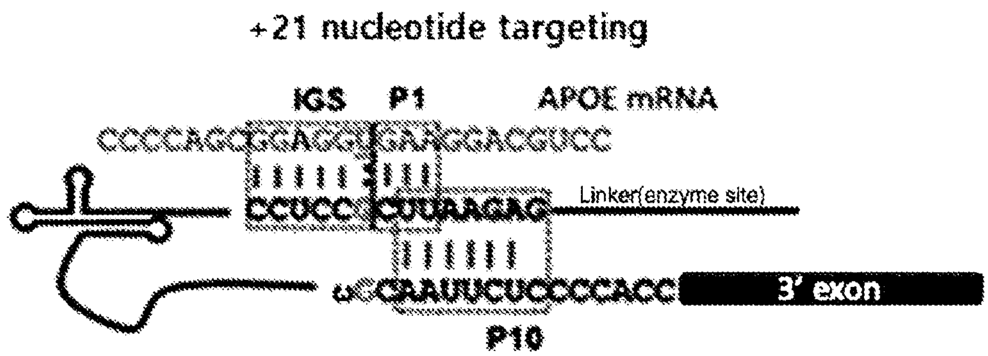
FIGS. 10A-10C are schematic diagramms of the structure of the trans-splicing ribozyme of the present invention.
Figure 10B:
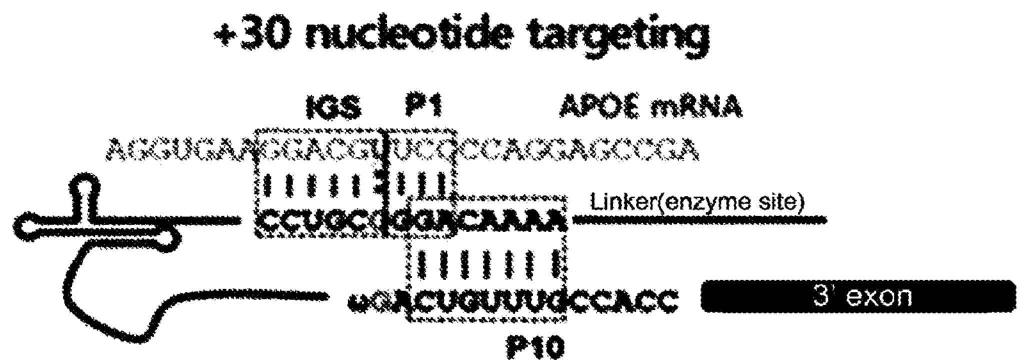
Figure 10C:
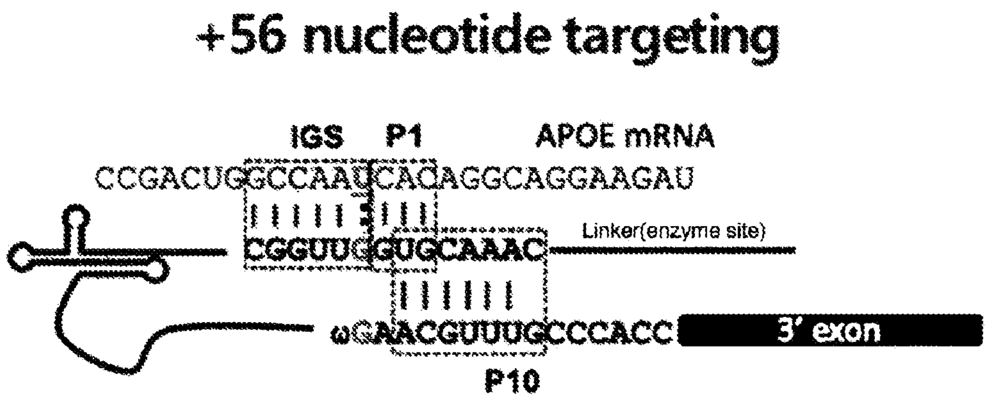

At the gene level, the trans-splicing product identification result was the same as the protein level identification result (FIG. 9B). It was identified that the reaction occurred exactly at the expected trans-splicing position as a result of sequencing of the trans-splicing product (FIG. 9C).

Hereinbefore, the specific portions of the contents of the present invention have been described in detail. Therefore, it is apparent to those having ordinary skill in the pertinent field that such specific technology is merely a preferable embodiment, and the scope of the present invention is not limited thereto. Accordingly, the substantial scope of the present invention is defined by the appended claims and their equivalents.

INDUSTRIAL APPLICABILITY

The APOE4 target trans-splicing ribozyme of the present invention can be used as a drug for the prevention or treatment of Alzheimer's disease by inhibiting the expression of APOE4 protein, which itself increases the onset of Alzheimer's disease. Since it is possible to induce the expression of a gene that lowers the onset of Alzheimer's disease by trans-splicing, it can be used as a platform for introducing a therapeutic gene for Alzheimer's disease.

The invention claimed is:

1. A trans-splicing ribozyme targeting an apolipoprotein E4 (APOE4) RNA sequence, wherein the trans-splicing ribozyme has a structure of 5'-internal guide sequence (IGS)-ribozyme core region-exon-3', wherein the IGS region consists of a nucleotide sequence of 6 to 10 nt in length and wherein the IGS region is selected from the group consisting of SEQ ID NO: 2,4, and 6.

2. The trans-splicing ribozyme of claim 1, wherein the IGS region consists of the nucleotide sequence of SEQ ID NO: 2.

3. The trans-splicing ribozyme of claim 1, wherein the trans-splicing ribozyme further includes an antisense sequence (AS) region of 10 nt to 200 nt in length capable of complementary binding to a portion of APOE4 RNA upstream of the IGS region.

4. The trans-splicing ribozyme of claim 3, wherein the IGS region consists of the nucleotide sequence of SEQ ID NO: 2, and the AS region has a length of 150 nt.

5. The trans-splicing ribozyme of claim 3, wherein the IGS region consists of the nucleotide sequence of SEQ ID NO: 4, and the AS region has a length of 50 nt.

6. The trans-splicing ribozyme of claim 3, wherein the IGS region and the AS region are linked to a random nucleotide sequence of 5 to 10 nt in length.

7. The trans-splicing ribozyme of claim 1, wherein the ribozyme core region includes the nucleotide sequence of SEQ ID NO: 7.

8. The trans-splicing ribozyme of claim 1, wherein the exon region includes a part or all of a nucleotide sequence encoding ApoE2 or ApoE3 christchurch mutation (R136S).

9. An expression vector capable of expressing the trans-splicing ribozyme of claim 1.

10. The expression vector of claim 9, wherein the expression vector further includes a promoter operably linked to a nucleotide sequence encoding the trans-splicing ribozyme.

11. The expression vector of claim 10, wherein the promoter is a neuron type-specific promoter.

12. The expression vector of claim 11, wherein the neuron type-specific promoter is a neuron-, astrocyte-, or oligodendrocyte-specific promoter.

13. A pharmaceutical composition for treating Alzheimer's disease comprising an adeno-associated virus vector capable of expressing the trans-splicing ribozyme of claim 1, or a gene delivery system containing the adeno-associated virus vector, wherein a nucleotide sequence encoding the trans-splicing ribozyme is operably linked to a neuron-specific promoter.

14. A method for treating Alzheimer's disease including administering to a subject the trans-splicing ribozyme of claim 1, a vector capable of expressing the same or a gene delivery system containing the vector, wherein administration is by intracerebral or intracisternal injection.

* * * * *

SEQUENCE LISTING

```
<160> NUMBER OF SEQ ID NOS: 36

<210> SEQ ID NO 1
<211> LENGTH: 6
<212> TYPE: RNA
<213> ORGANISM: Homo sapiens
<223> OTHER INFORMATION: +56 targeting region

<400> SEQUENCE: 1

gccaau                                                                 6
```

<210> SEQ ID NO 2
<211> LENGTH: 6
<212> TYPE: RNA
<213> ORGANISM: Artificial Sequence
<220> FEATURE:
<223> OTHER INFORMATION: IGS region of +56 targeting ribozyme

<400> SEQUENCE: 2 guuggc 6

<210> SEQ ID NO 3
<211> LENGTH: 6
<212> TYPE: RNA
<213> ORGANISM: Homo sapiens
<223> OTHER INFORMATION: +21 targeting region

<400> SEQUENCE: 3 ggaggu 6

<210> SEQ ID NO 4
<211> LENGTH: 6
<212> TYPE: RNA
<213> ORGANISM: Artificial Sequence
<220> FEATURE:
<223> OTHER INFORMATION: IGS region of +21 targeting ribozyme

<400> SEQUENCE: 4 gccucc 6

<210> SEQ ID NO 5
<211> LENGTH: 6
<212> TYPE: RNA
<213> ORGANISM: Homo sapiens
<223> OTHER INFORMATION: +30 targeting region

<400> SEQUENCE: 5 ggacgu 6

<210> SEQ ID NO 6
<211> LENGTH: 6
<212> TYPE: RNA
<213> ORGANISM: Artificial Sequence
<220> FEATURE:
<223> OTHER INFORMATION: IGS region of +30 targeting ribozyme

<400> SEQUENCE: 6 gcgucc 6

<210> SEQ ID NO 7
<211> LENGTH: 387
<212> TYPE: RNA
<213> ORGANISM: Artificial Sequence
<220> FEATURE:
<223> OTHER INFORMATION: Ribozyme* region

<400> SEQUENCE: 7
aaaaguuauc aggcaugcac cugguagcua gucuuuaaac caauagauug caucgguuua 60
aaaggcaaga ccgucaaauu gcgggaaagg ggucaacagc cguucaguac caagucucag 120
gggaaacuuu gagauggccu ugcaaagggu augguaauaa gcugacggac augguccuaa 180
ccacgcagcc aaguccuaag ucaacagauc uucuguugau auggaugcag uucacagacu 240
aaaugucggu cggggaagau guauucuucu cauaagauau agucggaccu cuccuuaaug 300

-continued ggagcuagcg gaugaaguga ugcaacacug gagccgcugg gaacuaauuu guaugcgaaa 360
guauauugau uaguuuugga guacucg 387

<210> SEQ ID NO 8
<211> LENGTH: 408
<212> TYPE: RNA
<213> ORGANISM: Artificial Sequence
<220> FEATURE:
<223> OTHER INFORMATION: +21 targeting ribozyme

<400> SEQUENCE: 8
gagaauucgc cuccaaaagu uaucaggcau gcaccuggua gcuagucuuu aaaccaauag 60
auugcaucgg uuuaaaaggc aagaccguca aauugcggga aaggggucaa cagccguuca 120
guaccaaguc ucaggggaaa cuuugagaug gccuugcaaa ggguauggua auaagcugac 180
ggacaugguc cuaaccacgc agccaagucc uaagucaaca gaucuucugu ugauauggau 240
gcaguucaca gacuaaaugu cggucgggga agauguauuc uucucauaag auauagucgg 300
accucuccuu aaugggagcu agcggaugaa gugaugcaac acuggagccg cugggaacua 360
auuuguaugc gaaaguauau ugauuaguuu uggaguacuc gcaauucu 408

<210> SEQ ID NO 9
<211> LENGTH: 410
<212> TYPE: RNA
<213> ORGANISM: Artificial Sequence
<220> FEATURE:
<223> OTHER INFORMATION: +30 targeting ribozyme

<400> SEQUENCE: 9
aaaacagggc guccaaaagu uaucaggcau gcaccuggua gcuagucuuu aaaccaauag 60
auugcaucgg uuuaaaaggc aagaccguca aauugcggga aaggggucaa cagccguuca 120
guaccaaguc ucaggggaaa cuuugagaug gccuugcaaa ggguauggua auaagcugac 180
ggacaugguc cuaaccacgc agccaagucc uaagucaaca gaucuucugu ugauauggau 240
gcaguucaca gacuaaaugu cggucgggga agauguauuc uucucauaag auauagucgg 300
accucuccuu aaugggagcu agcggaugaa gugaugcaac acuggagccg cugggaacua 360
auuuguaugc gaaaguauau ugauuaguuu uggaguacuc gacuguuuug 410

<210> SEQ ID NO 10
<211> LENGTH: 409
<212> TYPE: RNA
<213> ORGANISM: Artificial Sequence
<220> FEATURE:
<223> OTHER INFORMATION: +56 targeting ribozyme

<400> SEQUENCE: 10
caaacguggu uggcaaaagu uaucaggcau gcaccuggua gcuagucuuu aaaccaauag 60
auugcaucgg uuuaaaaggc aagaccguca aauugcggga aaggggucaa cagccguuca 120
guaccaaguc ucaggggaaa cuuugagaug gccuugcaaa ggguauggua auaagcugac 180
ggacaugguc cuaaccacgc agccaagucc uaagucaaca gaucuucugu ugauauggau 240
gcaguucaca gacuaaaugu cggucgggga agauguauuc uucucauaag auauagucgg 300
accucuccuu aaugggagcu agcggaugaa gugaugcaac acuggagccg cugggaacua 360
auuuguaugc gaaaguauau ugauuaguuu uggaguacuc gaacguuug 409

<210> SEQ ID NO 11
<211> LENGTH: 387

-continued

<212> TYPE: RNA
<213> ORGANISM: Homo sapiens
<223> OTHER INFORMATION: ApoE4 mRNA

<400> SEQUENCE: 11
aaaaguuauc aggcaugcac cugguagcua gucuuuaaac caauagauug caucgguuua 60
aaaggcaaga ccgucaaauu gcgggaaagg ggucaacagc cguucaguac caagucucag 120
gggaaacuuu gagauggccu ugcaaagggu augguaauaa gcugacggac augguccuaa 180
ccacgcagcc aaguccuaag ucaacagauc uucuguugau auggaugcag uucacagacu 240
aaaugucggu cggggaagau guauucuucu cauaagauau agucggaccu cuccuuaaug 300
ggagcuagcg gaugaaguga ugcaacacug gagccgcugg gaacuaauuu guaugcgaaa 360
guauauugau uaguuuugga guacucg 387

<210> SEQ ID NO 12
<211> LENGTH: 18
<212> TYPE: DNA
<213> ORGANISM: Artificial Sequence
<220> FEATURE:
<223> OTHER INFORMATION: RY-RT primer

<400> SEQUENCE: 12
atgtgctgca aggcgatt 18

<210> SEQ ID NO 13
<211> LENGTH: 26
<212> TYPE: DNA
<213> ORGANISM: Artificial Sequence
<220> FEATURE:
<223> OTHER INFORMATION: ApoE4 forward primer

<400> SEQUENCE: 13
ctactcagcc ccagcggagg tgaagg 26

<210> SEQ ID NO 14
<211> LENGTH: 19
<212> TYPE: DNA
<213> ORGANISM: Artificial Sequence
<220> FEATURE:
<223> OTHER INFORMATION: RY-TS primer

<400> SEQUENCE: 14
tgtaaaacga cggccagtg 19

<210> SEQ ID NO 15
<211> LENGTH: 25
<212> TYPE: DNA
<213> ORGANISM: Artificial Sequence
<220> FEATURE:
<223> OTHER INFORMATION: RT primer

<400> SEQUENCE: 15
cccatatcgt ttcatagctt ctgcc 25

<210> SEQ ID NO 16
<211> LENGTH: 19
<212> TYPE: DNA
<213> ORGANISM: Artificial Sequence
<220> FEATURE:
<223> OTHER INFORMATION: forward primer

<400> SEQUENCE: 16
cagcggaggt gaaggacgt 19

<210> SEQ ID NO 17
<211> LENGTH: 23
<212> TYPE: DNA
<213> ORGANISM: Artificial Sequence
<220> FEATURE:
<223> OTHER INFORMATION: reverse primer

<400> SEQUENCE: 17
atgttcacct cgatatgtgc atc 23

<210> SEQ ID NO 18
<211> LENGTH: 6
<212> TYPE: RNA
<213> ORGANISM: Artificial Sequence
<220> FEATURE:
<223> OTHER INFORMATION: random sequence
<220> FEATURE:
<221> NAME/KEY: variation
<222> LOCATION: (2)..(6)
<223> OTHER INFORMATION: n is any one of A, G, C, and U

<400> SEQUENCE: 18 gnnnnn 6

<210> SEQ ID NO 19
<211> LENGTH: 18
<212> TYPE: DNA
<213> ORGANISM: Artificial Sequence
<220> FEATURE:
<223> OTHER INFORMATION: ribozyme specific RT primer

<400> SEQUENCE: 19
atgtgctgca aggcgatt 18

<210> SEQ ID NO 20
<211> LENGTH: 18
<212> TYPE: DNA
<213> ORGANISM: Artificial Sequence
<220> FEATURE:
<223> OTHER INFORMATION: ribozyme specific 3' primer

<400> SEQUENCE: 20
tgtaaacgac ggccagtg 18

<210> SEQ ID NO 21
<211> LENGTH: 70
<212> TYPE: RNA
<213> ORGANISM: Homo sapiens
<223> OTHER INFORMATION: APOE4 RNA

<400> SEQUENCE: 21
gccaaucaca ggcaggaaga ugaagguucu gugggcugcg uugcugguca cauuccuggc 60
aggaugccag 70

<210> SEQ ID NO 22
<211> LENGTH: 6
<212> TYPE: RNA
<213> ORGANISM: Artificial Sequence
<220> FEATURE:
<223> OTHER INFORMATION: +56 targeting ribozyme Internal Guide sequence
(IGS)

<400> SEQUENCE: 22 guuggc 6

-continued

<210> SEQ ID NO 23
<211> LENGTH: 50
<212> TYPE: DNA
<213> ORGANISM: Artificial Sequence
<220> FEATURE:
<223> OTHER INFORMATION: Trans-splicing product by +56 targeting ribozyme

<400> SEQUENCE: 23
ccttccccag gagccgactg gccaatcgag ggggtacccg gggatcctct 50

<210> SEQ ID NO 24
<211> LENGTH: 74
<212> TYPE: RNA
<213> ORGANISM: Homo sapiens
<223> OTHER INFORMATION: APOE4 RNA

<400> SEQUENCE: 24
acuggccaau cacaggcagg aagaugaagg uucugugggc ugcguugcug gucacauucc 60
uggcaggaug ccag 74

<210> SEQ ID NO 25
<211> LENGTH: 9
<212> TYPE: RNA
<213> ORGANISM: Artificial Sequence
<220> FEATURE:
<223> OTHER INFORMATION: +56 targeting ribozyme Internal Guide sequence (IGS) include P1

<400> SEQUENCE: 25 gugguuggc 9

<210> SEQ ID NO 26
<211> LENGTH: 59
<212> TYPE: DNA
<213> ORGANISM: Artificial Sequence
<220> FEATURE:
<223> OTHER INFORMATION: Trans-splicing product by +56 targeting ribozyme

<400> SEQUENCE: 26
acgtccttcc ccaggagccg actggccaat aacgtttgcc caccatggaa gacgccaaa 59

<210> SEQ ID NO 27
<211> LENGTH: 52
<212> TYPE: DNA
<213> ORGANISM: Artificial Sequence
<220> FEATURE:
<223> OTHER INFORMATION: Trans-splicing product by +21 targeting ribozyme

<400> SEQUENCE: 27
ccttctactc agccccagcg gaggtcaatt ctccccacca tggaagacgc ca 52

<210> SEQ ID NO 28
<211> LENGTH: 24
<212> TYPE: RNA
<213> ORGANISM: Homo sapiens
<223> OTHER INFORMATION: APOE4 RNA

<400> SEQUENCE: 28
ccccagcgga ggugaaggac gucc 24

<210> SEQ ID NO 29
<211> LENGTH: 14

-continued

<212> TYPE: RNA
<213> ORGANISM: Artificial Sequence
<220> FEATURE:
<223> OTHER INFORMATION: +21 targeting ribozyme IGS include P1, P10 sequence

<400> SEQUENCE: 29
gagaauucgc cucc 14

<210> SEQ ID NO 30
<211> LENGTH: 15
<212> TYPE: RNA
<213> ORGANISM: Artificial Sequence
<220> FEATURE:
<223> OTHER INFORMATION: +21 targeting ribozyme P10 sequence

<400> SEQUENCE: 30
gcaauucucc ccacc 15

<210> SEQ ID NO 31
<211> LENGTH: 27
<212> TYPE: RNA
<213> ORGANISM: Homo sapiens
<223> OTHER INFORMATION: APOE4 RNA

<400> SEQUENCE: 31
aggugaagga cguuccccag gagccga 27

<210> SEQ ID NO 32
<211> LENGTH: 14
<212> TYPE: RNA
<213> ORGANISM: Artificial Sequence
<220> FEATURE:
<223> OTHER INFORMATION: +30 targeting ribozyme IGS include P1, P10 sequence

<400> SEQUENCE: 32
aaaacagggc gucc 14

<210> SEQ ID NO 33
<211> LENGTH: 14
<212> TYPE: RNA
<213> ORGANISM: Artificial Sequence
<220> FEATURE:
<223> OTHER INFORMATION: +30 targeting ribozyme P10 sequence

<400> SEQUENCE: 33
gacuguuugc cacc 14

<210> SEQ ID NO 34
<211> LENGTH: 28
<212> TYPE: RNA
<213> ORGANISM: Homo sapiens
<223> OTHER INFORMATION: APOE4 RNA

<400> SEQUENCE: 34
ccgacuggcc aaucacaggc aggaagau 28

<210> SEQ ID NO 35
<211> LENGTH: 14
<212> TYPE: RNA
<213> ORGANISM: Artificial Sequence
<220> FEATURE:
<223> OTHER INFORMATION: +56 targeting ribozyme IGS include P1, P10 sequence

<400> SEQUENCE: 35

-continued

```
caaacguggu uggc                                                    14


<210> SEQ ID NO 36
<211> LENGTH: 15
<212> TYPE: RNA
<213> ORGANISM: Artificial Sequence
<220> FEATURE:
<223> OTHER INFORMATION: +56 targeting ribozyme P10 sequence

<400> SEQUENCE: 36

gaacguuugc ccacc                                                   15
```